(12) United States Patent
Harada

(10) Patent No.: US 7,574,151 B2
(45) Date of Patent: Aug. 11, 2009

(54) SMOKE DETECTING DEVICE, FLASH FUSING DEVICE, IMAGE FORMING DEVICE AND SMOKE DETECTING METHOD

(75) Inventor: Masaaki Harada, Ebina (JP)

(73) Assignee: Fuji Xerox Co., Ltd., Tokyo (JP)

( * ) Notice: Subject to any disclaimer, the term of this patent is extended or adjusted under 35 U.S.C. 154(b) by 210 days.

(21) Appl. No.: 11/790,935

(22) Filed: Apr. 30, 2007

(65) Prior Publication Data

US 2008/0069575 A1    Mar. 20, 2008

(30) Foreign Application Priority Data

Sep. 14, 2006    (JP) ............... 2006-249293

(51) Int. Cl.
*G03G 15/20* (2006.01)
*G03G 21/20* (2006.01)

(52) U.S. Cl. .............. 399/33; 399/91; 399/94; 399/336

(58) Field of Classification Search .......... 399/33, 399/91, 94, 336, 337
See application file for complete search history.

(56) References Cited

U.S. PATENT DOCUMENTS 5,477,218 A * 12/1995 Manmoto et al. ........... 340/630

2005/0286916 A1* 12/2005 Nakazato et al. ............. 399/16
2007/0097372 A1*  5/2007 Itagaki ....................... 356/437

FOREIGN PATENT DOCUMENTS

JP      A 7-319322        5/1994

OTHER PUBLICATIONS

Machine Translation of JP 07-319322 A.*

* cited by examiner

*Primary Examiner*—David M Gray
*Assistant Examiner*—Gregory H Curran
(74) *Attorney, Agent, or Firm*—Margaret A. Burke; Sheldon J. Moss

(57) ABSTRACT

A smoke detecting device including: a light-emitting portion that emits light; a light-receiving portion that receives scattered light resulting from the light which the light-emitting portion emits being scattered by smoke generated from a recording medium on which flash-light is irradiated from a flash fusing device; and a judging section that acquires a light amount signal of the received light, from the light-receiving portion, and that judges, on the basis of the light amount signal, whether or not smoke has been generated from the recording medium on which flash-light is irradiated from the flash fusing device, the light that the light-emitting portion emits passing through a space between the flash fusing device and the recording medium, is provided.

18 Claims, 16 Drawing Sheets

FIG.5A
FIG.5B
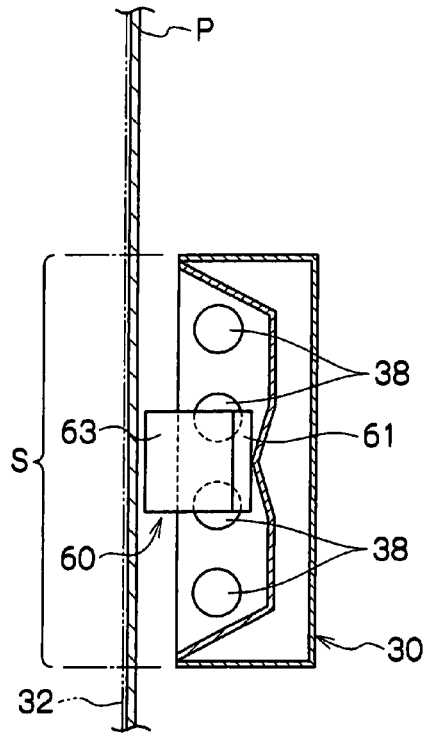
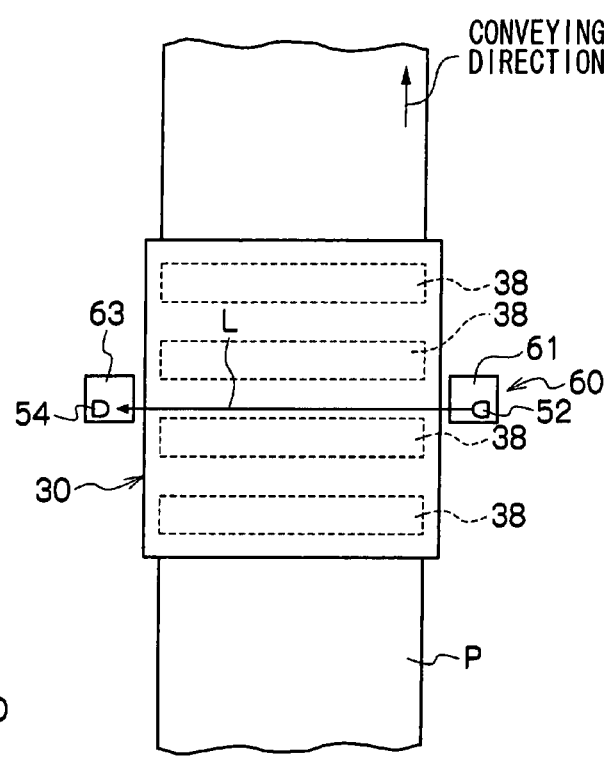

AT TIME WHEN SMOKE IS NOT GENERATED

AT TIME WHEN SMOKE IS GENERATED

SMOKE DETECTING DEVICE, FLASH FUSING DEVICE, IMAGE FORMING DEVICE AND SMOKE DETECTING METHOD

CROSS-REFERENCE TO RELATED APPLICATION

This application is based on and claims priority under 35 USC 119 from Japanese Patent Application No. 2006-249293 filed Sep. 14, 2006.

BACKGROUND

1. Technical Field

The present invention relates to a smoke detecting device, a flash fusing device, an image forming device and a smoke detecting method.

2. Related Art

Electrophotographic image forming devices, which illuminate flash-light onto a toner image and fix the toner image on a recording medium, are known as image forming devices. This fixing method has the advantage that, because there is no contact with the toner image at the time of fixing, there is little deterioration in image quality due to the fixing.

Further, there are known electrophotographic image forming devices which, by using radiant heat, fix a toner image onto a recording medium in a non-contact manner.

SUMMARY

A smoke detecting device of an aspect of the present invention includes: a light-emitting portion that emits light; a light-receiving portion that receives scattered light resulting from the light which the light-emitting portion emits being scattered by smoke generated from a recording medium on which flash-light is irradiated from a flash fusing device; and a judging section that acquires a light amount signal of the received light, from the light-receiving portion, and that judges, on the basis of the light amount signal, whether or not smoke has been generated from the recording medium on which flash-light is irradiated from the flash fusing device, the light that the light-emitting portion emits passing through a space between the flash fusing device and the recording medium.

BRIEF DESCRIPTION OF THE DRAWINGS

Exemplary embodiments of the invention will be described in detail with reference to the following figures, wherein:

FIG. 5A is a front view showing an example of a position at which the smoke detecting device is disposed in a structure in which the flash fusing device relating to the present exemplary embodiment illuminates flash-light from a side surface side of the recording medium, and FIG. 5B is a side view showing the example of the position at which the smoke detecting device is disposed in the structure in which the flash fusing device relating to the present exemplary embodiment illuminates flash-light from the side surface side of the recording medium;

FIG. 8A shows a case in which the temperature of the flash lamp is 500 K, FIG. 8B shows a case in which the temperature of the flash lamp is 1000 K, and FIG. 8C shows a case in which the temperature of the flash lamp is 1500 K;

FIG. 10A shows a signal pattern at a time when no smoke is generated, and FIG. 10B shows a signal pattern at a time when smoke is generated;

FIG. 15A shows a signal pattern at a time when no smoke is generated, and FIG. 15B shows a signal pattern at a time when smoke is generated; FIG. 16A shows a case in which the respective sets of the light-emitting portion and the light-receiving portion are disposed along a direction orthogonal to the conveying direction, and FIG. 16B shows a case in which the respective sets of the light-emitting portion and the light-receiving portion are disposed in a grid form.

DETAILED DESCRIPTION

Examples of exemplary embodiments relating to the present invention will be described hereinafter on the basis of the drawings. First, the overall structure of an image forming device relating to the present exemplary embodiment will be described.

Figure 1:
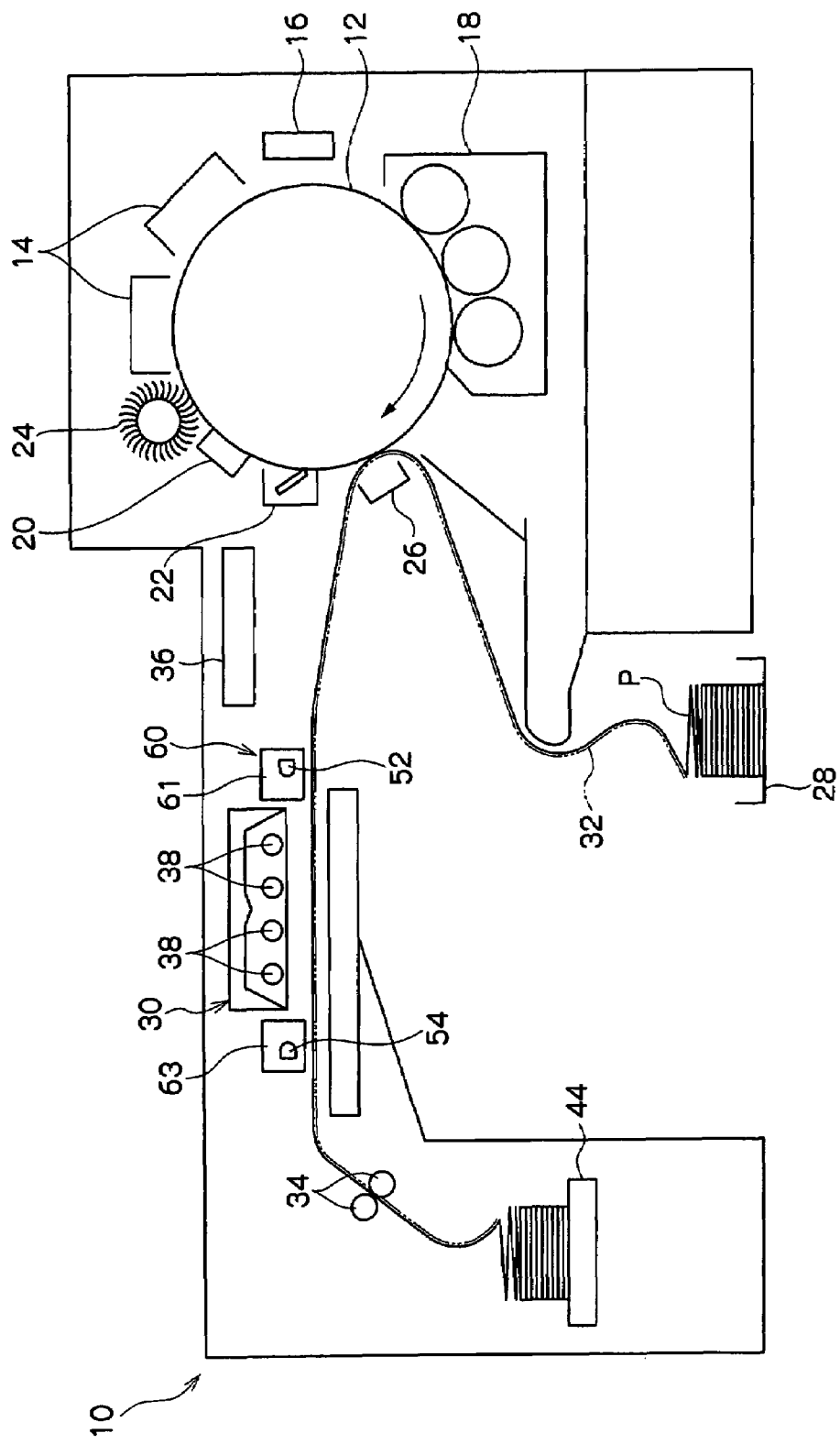
FIG. 1 is a drawing showing the overall structure of an image forming device relating to an exemplary embodiment of the present invention.

As shown in FIG. 1, an image forming device 10 relating to the present exemplary embodiment has a recording medium accommodating section 28 which accommodates a recording medium P. In the present exemplary embodiment, a continuous sheet, which is formed in the shape of an elongated strip, is used as the recording medium P. After images are formed thereon, the continuous sheet is made into sheets which are cut to a predetermined size. Note that it suffices for the recording medium P to be a recording medium on which images are formed, and, for example, sheets which are cut to a predetermined size in advance (so-called cut sheets) may be used.

The recording medium P is accommodated at the recording medium accommodating section 28 in a state of being folded-over. The accommodated recording medium P is conveyed by a conveying device 34 along a conveying path 32 which is formed within the image forming device 10.

In the present exemplary embodiment, a pair of conveying rollers, which rotate while nipping the recording medium P are used as the conveying device 34. Note that it suffices for the conveying device 34 to be a conveying device which conveys the recording medium P, and it may be a conveying device which conveys the recording medium P by causing pins to engage with plural feed holes which are formed along the longitudinal direction in the both transverse direction end portions (side end portions) of the recording medium P.

A photosensitive drum 12, which rotates in a predetermined direction (clockwise direction in FIG. 1), and a flash fusing device 30, which is provided with flash lamps 38 and which serves as a flash fusing device in which the flash lamps 38 flash light, are provided along the conveying path 32 at which the recording medium P is conveyed, in that order from the conveying direction upstream side.

A charging device 14 which charges the surface of the photosensitive drum 12, an exposure device 16 which exposes the charged photosensitive drum 12 and forms an electrostatic latent image on the surface of the photosensitive drum 12, a developing device 18 which develops the electrostatic latent image formed on the surface of the photosensitive drum 12 so as to form a toner image, a cleaning blade 22 which cleans-off the residual toner remaining on the photosensitive drum 12, a destaticizing device 20 which destaticizes the surface of the photosensitive drum 12, and a cleaner brush 24 cleaning-off the residual toner remaining on the photosensitive drum 12, are disposed at the periphery of the photosensitive drum 12, in that order from the upstream side in the rotating direction of the photosensitive drum 12.

A transfer device 26, which transfers the toner image formed on the photosensitive drum 12 onto the recording medium P, is provided at a position opposing the photosensitive drum 12, with the conveying path 32 nipped therebetween.

The toner image which is transferred on the recording medium P is fixed by the flash fusing device 30 by causing the flash lamps 38 to emit light such that flash-light is illuminated onto the recording medium P. A driving control section 36, which controls the driving of the flash fusing device 30, is connected to the flash fusing device 30. The light amounts and the light-emission timings of the flash lamps 38 are controlled by the driving control section 36 by controlling the amount of voltage and the amount of current supplied to the flash fusing device 30, the timing of the supply thereof, and the like.

A smoke detecting device 60, which senses smoke which is generated from the recording medium onto which the flash-light is illuminated from the flash fusing device 30, is provided at the flash fusing device 30.

The recording medium P, on which the toner image is fixed by the flash fusing device 30, is conveyed further toward the downstream side, and is folded-over and accommodated in a recording medium accommodating section 44 which accommodates the recording medium P.

The smoke detecting device 60, which senses smoke which is generated from the recording medium onto which flash-light is illuminated from the flash fusing device 30, will be described next.

In an illumination region S in which flash-light is illuminated from the flash fusing device 30, due to, for example, the recording medium P becoming jammed at the conveying path 32 and stopping in the illumination region S, or due to a residual piece of the recording medium P stopping in the illumination region S, or due to malfunctioning of the flash fusing device 30, or the like, there is the possibility that the flash-light from the flash lamps 38 will be illuminated plural times onto the recording medium P, and that smoke will be generated from the recording medium P in the illumination region S.

Figure 2A:
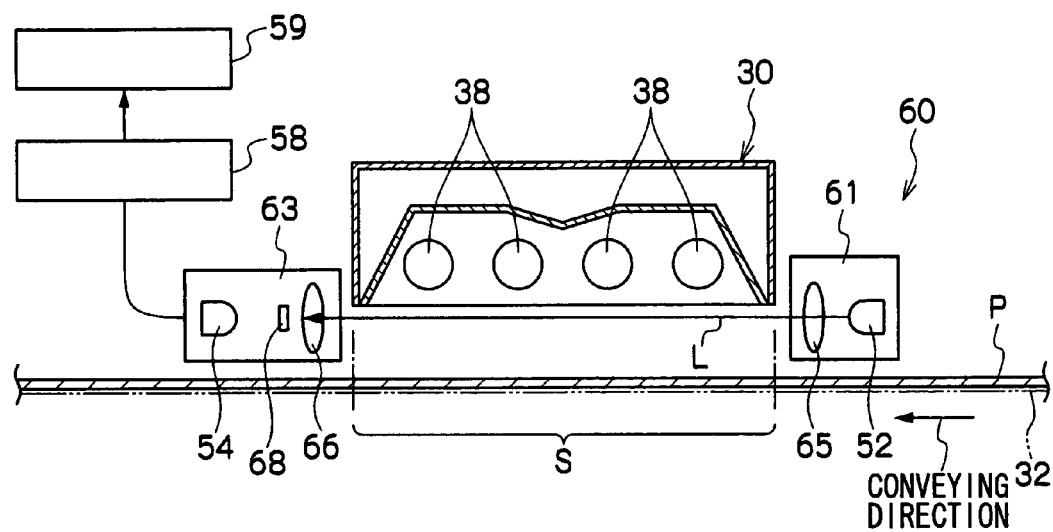
FIG. 2A is a side view showing the structure of a smoke detecting device relating to the present exemplary embodiment.
Figure 2B:
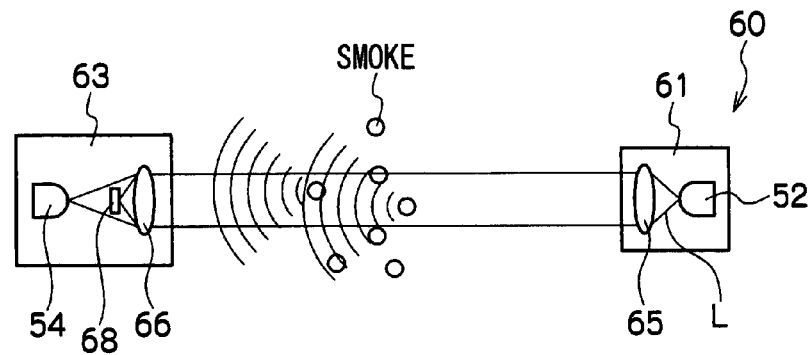
FIG. 2B is a plan view showing the structure of the smoke detecting device relating to the present exemplary embodiment.

The smoke detecting device 60 relating to the present exemplary embodiment detects smoke which is generated at the illumination region S. As shown in FIG. 2A and FIG. 2B, the smoke detecting device 60 is provided with a light-emitting device 61 which emits light, and a light-receiving device 63 which receives the light. The light-emitting device 61 is disposed at the conveying direction upstream side as seen from the flash fusing device 30. The light-receiving device 63 is disposed at the conveying direction downstream side as seen from the flash fusing device 30, and the light-receiving device 63 is disposed so as to oppose the light-emitting device 61, with the flash fusing device 30 therebetween. The light-emitting device 61 and the light-receiving device 63 are disposed at the outer side of the illumination region S at which the flash fusing device 30 illuminates the flash-light, i.e., at positions at which the flash-light from the flash fusing device 30 is not illuminated.

The light-emitting device 61 and the light-receiving device 63 are disposed in close vicinity to the flash fusing device 30. Note that the positions of the light-emitting device 61 and the light-receiving device 63 are positions at which flash-light is not illuminated from the flash fusing device 30, and positions which are closest to the flash fusing device 30 are preferable.

The light-emitting device 61 is provided with a light-emitting portion 52 which illuminates light L, and a lens 65 serving as an optical element.

The light-emitting portion 52 emits the light L from the conveying direction upstream side toward the downstream side, along the conveying path 32 at which the recording medium P is conveyed. The light L emitted by the light-emitting section 52 passes-through between the flash fusing device 30 and the conveying path 32, and passes-through above the illumination region S illuminated by the flash fusing device 30. For example, a light-emitting diode (LED), a laser diode (LD), or another light-emitting element can be used as the light-emitting portion 52.

The lens 65 is provided at the light L exiting side of the light-emitting portion 52, and, as shown in FIG. 2B, makes the light L which the light-emitting portion 52 emits into parallel light.

A light-receiving portion 54 which receives light, a condenser lens 66 serving as an optical element, and a light-shielding plate 68 serving as a light-shielding member, are provided at the light-receiving device 63.

The light-receiving portion 54 receives the scattered light of the light L which scatters due to smoke generated from the recording medium P. The light-receiving portion 54 is disposed at a position opposing the light-emitting portion 52, and receives the scattered light which scatters toward the side opposite the side at which the light-emitting portion 52 is at, i.e., receives the scattered light which scatters forward. For example, a photodiode, a PIN photodiode, or another light-receiving element can be used as the light-receiving portion 54.

The light-shielding plate 68 is provided at the light-receiving surface side at which the light-receiving portion 54 receives light, i.e., at the incident side where the light is incident, and absorbs and shields the light. The condenser lens 66 is provided between the light-emitting portion 52 and the light-shielding plate 68, and collects the light emitted by the light-emitting portion 52. In this way, among the light L which is emitted from the light-emitting portion 52, the direct light which passes-through without scattering is collected, by the condenser lens 66, at the light-shielding plate 68, and is shielded at the light-shielding plate 68, and is not incident on the light-receiving portion 54. Note that the angle at which the light L, which scatters due to the smoke generated from the recording medium P, is incident on the condenser lens 66 is different from that of the direct light, and the light L which scatters is collected at the light-receiving portion 54.

A processing device 58 is connected to the light-receiving device 63. The processing device 58 serves as a judging section which acquires, from the light-receiving portion 54, a light amount signal of the light received by light-receiving portion 54, and judges whether or not smoke is generated.

Figure 3A:
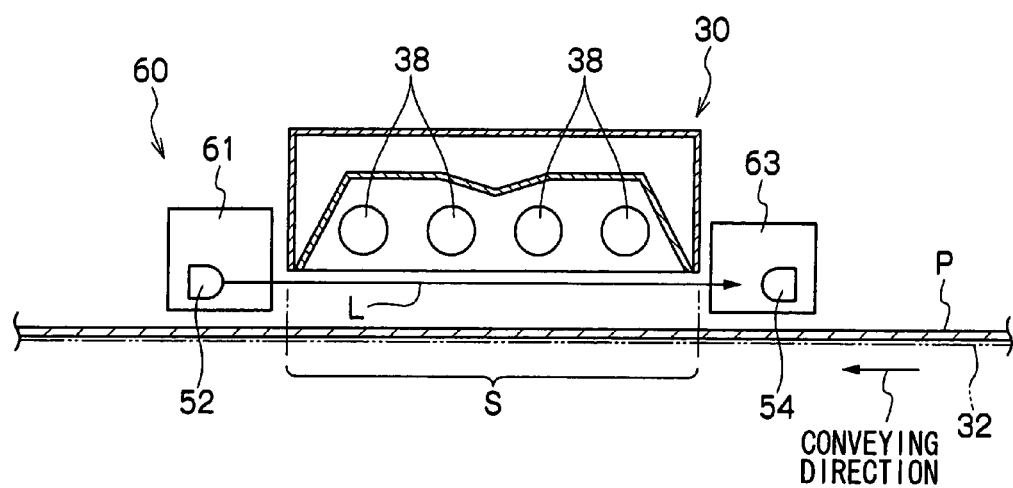
FIG. 3A is a drawing showing a case in which the positions at which a light-emitting device and a light-receiving device are disposed are reversed in the smoke detecting device relating to the present exemplary embodiment.

Note that, in the above-described structure, the light-emitting device 61 is disposed at the conveying direction upstream side as seen from the flash fusing device 30, and the light-receiving device 63 is disposed at the conveying direction downstream side as seen from the flash fusing device 30. However, as shown in FIG. 3A, the light-emitting device 61 may be disposed at the conveying direction downstream side as seen from the flash fusing device 30, and the light-receiving device 63 may be disposed at the conveying direction upstream side as seen from the flash fusing device 30. In this structure, the light L from the light-emitting portion 52 of the light-emitting device 61 is emitted from the conveying direction downstream side toward the light-receiving portion 54 of the light-receiving device 63 which is at the conveying direction upstream side.

Figure 3B:
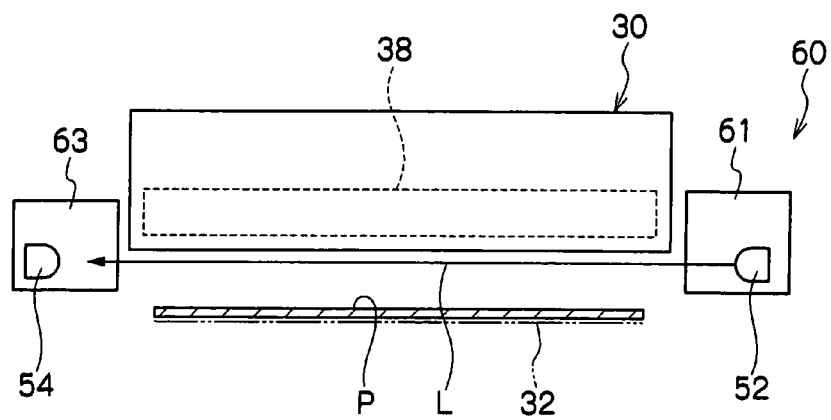
FIG. 3B is a drawing showing a case in which the light-emitting device and the light-receiving device are disposed along a direction orthogonal to a conveying direction in the smoke detecting device relating to the present exemplary embodiment.

Further, as shown in FIG. 3B, the light-emitting device 61 may be disposed at one side in the direction orthogonal to the conveying direction as seen from the flash fusing device 30, and the light-receiving device 63 may be disposed at the other side in the direction orthogonal to the conveying direction as seen from the flash fusing device 30. In this structure, the light L from the light-emitting portion 52 of the light-emitting device 61 is emitted along the direction orthogonal to the conveying direction.

Figure 4:
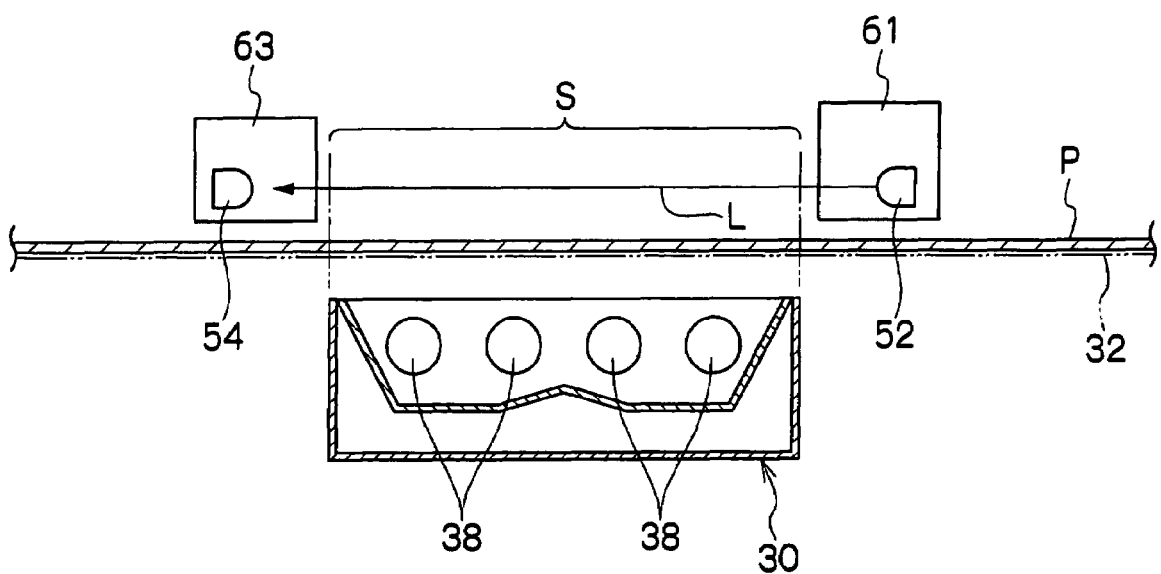
FIG. 4 is a drawing showing an example of a position at which the smoke detecting device is disposed in a structure in which a flash fusing device relating to the present exemplary embodiment illuminates flash-light from a bottom surface side of a recording medium.

Further, as shown in FIG. 4, in a structure in which the flash fusing device 30 illuminates flash-light upward onto the bottom surface of the recording medium P, the light-emitting device 61 and the light-receiving device 63 may be disposed opposingly at the upper side of the conveying path 32. The light-emitting device 61 and the light-receiving device 63 are disposed at the outer side of the illumination region S where the flash fusing device 30 emits flash-light, i.e., at positions where the flash-light from the flash fusing device 30 is not illuminated. In this structure, the light L which the light-emitting portion 52 emits does not pass-through between the flash fusing device 30 and the conveying path 32, but passes-through above the illumination region S where the flash-light is illuminated from the flash fusing device 30 onto the recording medium P.

As shown in FIG. 5A and FIG. 5B, in a structure in which the recording medium P is conveyed in a vertical direction and the flash fusing device 30 illuminates flash-light onto one side surface of the recording medium P, the light-emitting device 61 and the light-receiving device 63 may be disposed opposingly at the transverse side of the flash fusing device 30. In this structure, the light-emitting device 61 and the light-receiving device 63 are disposed along a direction orthogonal to the conveying direction, and the light L from the light-emitting portion 52 of the light-emitting device 61 is emitted along the direction orthogonal to the conveying direction.

Figure 6A:
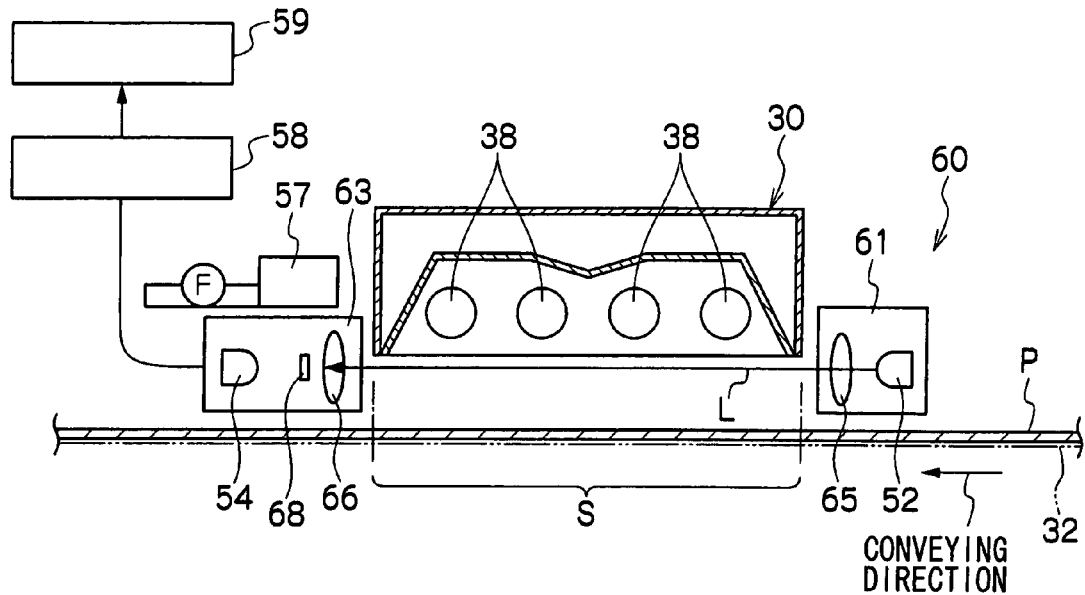
FIG. 6A is a side view showing an illuminating direction of light emitted by a light-emitting portion in a case in which the flash fusing device relating to the present exemplary embodiment has a ventilating device.
Figure 6B:
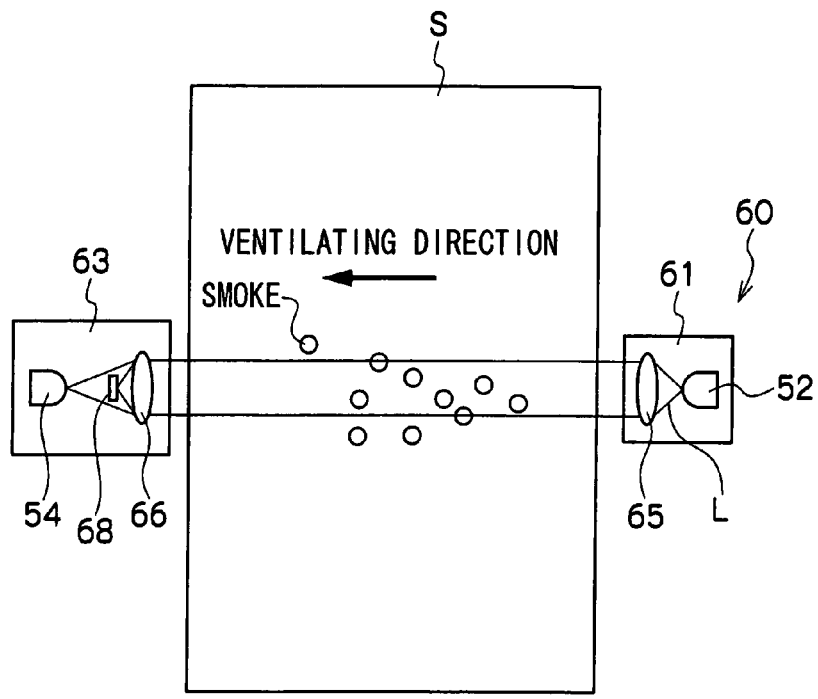
FIG. 6B is a plan view showing the illuminating direction of light emitted by the light-emitting portion in the structure in which the flash fusing device relating to the present exemplary embodiment has the ventilating device.

Further, as shown in FIG. 6A, in the flash fusing device 30 having a blower device (a ventilating device) 57 which sends air to the illumination region S, as shown in FIG. 6B, the light-emitting portion 52 emits the light L along the blowing direction. In this structure, as the blower device 57, a suction device which draws-in air by a fan is disposed at the conveying direction downstream side of the flash fusing device 30. In this way, wind is generated from the conveying direction upstream side of the flash fusing device 30 toward the conveying direction downstream side, and air is sent to the illumination region S. Note that a structure may be used in which a blower device, which sends air toward the conveying direction downstream side, is provided at the conveying direction upstream side of the flash fusing device 30.

In accordance with this structure, the smoke generated from the recording medium P is made to flow along the optical axis direction of the light L emitted by the light-emitting portion 52. Smoke particles exist for a long time on the optical path, and the scattered light is efficiently incident on the light-receiving portion 54.

A modified example, in which the structure of the smoke detecting device 60 relating to the present exemplary embodiment is modified, will be described next.

Figure 7A:
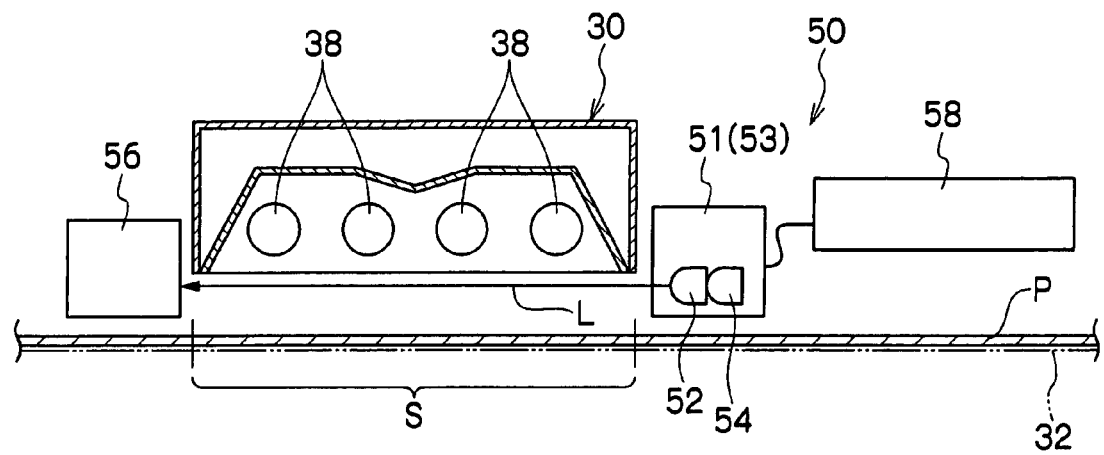
FIG. 7A is a side view showing a modified example of the smoke detecting device relating to the present exemplary embodiment.
Figure 7B:
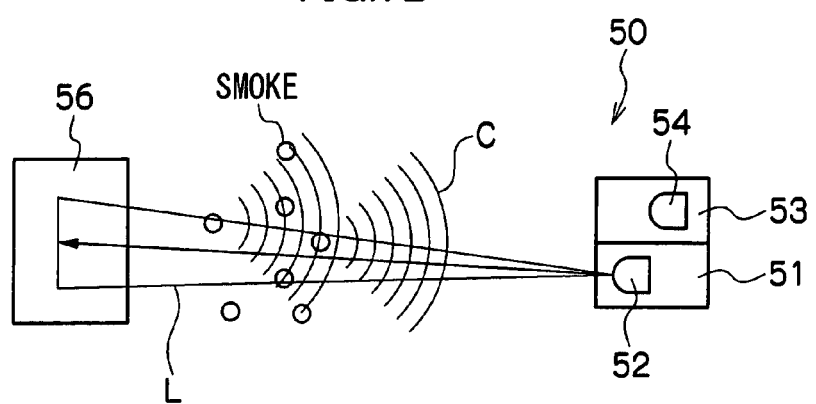
FIG. 7B is a side view showing the modified example of the smoke detecting device relating to the present exemplary embodiment.

As shown in FIG. 7B, a smoke detecting device 50, which serves as a modified example of the smoke detecting device 60, is structured to include a light-emitting device 51 which emits light and a light-receiving device 53 which receives light.

As shown in FIG. 7A, the light-emitting device 51 and the light-receiving device 53 are provided at the conveying direction upstream side of the flash fusing device 30, and are disposed at the outer side of the illumination region S, i.e., at positions at which the flash-light from the flash fusing device 30 is not illuminated. Further, the light-emitting device 51 and the light-receiving device 53 are provided in close vicinity to the flash fusing device 30. Note that the positions of the light-emitting device 51 and the light-receiving device 53 are desirably positions which are closest to the flash fusing device 30 at positions where flash-light is not illuminated from the flash fusing device 30.

As shown in FIG. 7A and FIG. 7B, the light-emitting device 51 is provided with the light-emitting portion 52 which emits the light L along the conveying path 32 at which the recording medium P is conveyed.

For example, a light-emitting diode (LED), a laser diode (LD) or another light-emitting element can be used as the light-emitting portion 52.

The light L emitted from the light-emitting portion 52 passes-through between the flash fusing device 30 and the recording medium P, and passes-through above the illumination region where light is illuminated from the flash fusing device 30.

The light-receiving device 53 is provided with the light-receiving portion 54 which receives scattered light which scatters when the light emitted from the light-emitting portion 52 hits smoke generated from the recording medium P. The light-receiving portion 54 receives scattered light which scatters toward the side where the light-emitting portion 52 is, i.e., scattered light which scatters backward.

For example, a photodiode, a PIN photodiode, or another light-receiving element can be used as the light-receiving portion 54.

The processing device 58 is connected to the light-receiving device 53. The processing device 58 serves as a judging section which acquires, from the light-receiving portion 54, a light amount signal of the light received by light-receiving portion 54, and judges whether or not smoke is generated. The light amount signal which the processing device 58 acquires expresses the amount of light which the light-receiving portion 54 receives.

A light absorbing device 56, which absorbs light which the light-emitting portion 52 emits, is disposed so as to oppose the light-emitting portion 52 at the conveying direction downstream side as seen from the flash fusing device 30. The light absorbing device 56 absorbs, among the light emitted by the light-emitting portion 52, the light which passes-through without scattering, and eliminates the reflected light which acts as a noise component. In this way, only the scattered light, which scatters upon hitting smoke, is incident on the light-receiving portion 54.

As with the positional relationship of the light-emitting device 61 and the light-receiving device 63 in the case of the smoke detecting device 60, in the smoke detecting device 50 as well, the light-emitting device 51 and the light-receiving device 53 may be disposed at the conveying direction downstream side as seen from the flash fusing device 30, and the light absorbing device 56 may be disposed at the conveying direction upstream side as seen from the flash fusing device 30 (refer to FIG. 3A).

Further, as with the positional relationship of the light-emitting device 61 and the light-receiving device 63 in the case of the smoke detecting device 60, the light-emitting device 51 and the light-receiving device 53 may be disposed at one side in a direction orthogonal to the conveying direction as seen from the flash fusing device 30, and the light absorbing device 56 may be disposed at the other side in the direction orthogonal to the conveying direction as seen from the flash fusing device 30 (refer to FIG. 3B).

As shown in FIG. 4, in a structure in which the flash fusing device 30 illuminates flash-light upward onto the bottom surface of the recording medium P, the light-emitting device 51 and the light-receiving device 53 on the one hand, and the light absorbing device 56 on the other hand, may be disposed opposingly at the upper side of the conveying path 32.

As shown in FIG. 5A and FIG. 5B, in a structure in which the recording medium P is conveyed in a vertical direction and the flash fusing device 30 illuminates flash-light onto one side surface of the recording medium P, the light-emitting device 51 and the light-receiving device 53 on the one hand, and the light absorbing device 56 on the other hand, may be disposed opposingly at the transverse side of the flash fusing device 30.

Moreover, as shown in FIG. 6A, in the flash fusing device 30 which is provided with the blower device 57 which sends air to the illumination region S, the light-emitting portion 52 is structured so as to emit the light L along the ventilating direction (refer to FIG. 6B).

The spectral characteristics of the light which the light-emitting portion 52 emits and the light which the light-receiving portion 54 receives will be described next.

In the flash fusing device 30 relating to the present exemplary embodiment, a light of the infrared radiation region is always irradiated from the high-temperature portion of the flash lamp 38. Further, due to the flash lamp 38 repeating the emission of light, the electrode portions reach a high-temperature, and visible light as well is irradiated. These irradiated lights become flares and stray lights and work as noise components with respect to the light-receiving portion 54. Further, the light, other than the scattered light which scatters by the smoke, becomes noise in the smoke detection with respect to the light-receiving portion 54.

Figure 8A:
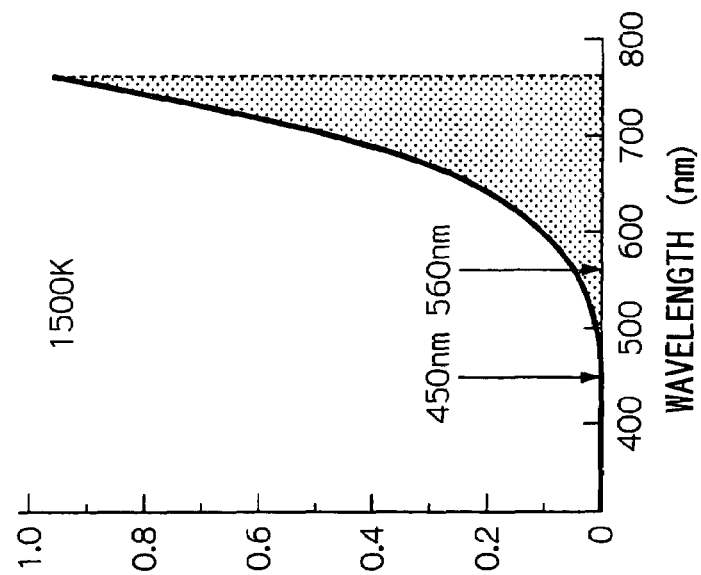
FIGS. 8A, 8B, 8C are drawings showing the wavelength of a light beam irradiated from a flash lamp relating to the present exemplary embodiment, where
Figure 8B:
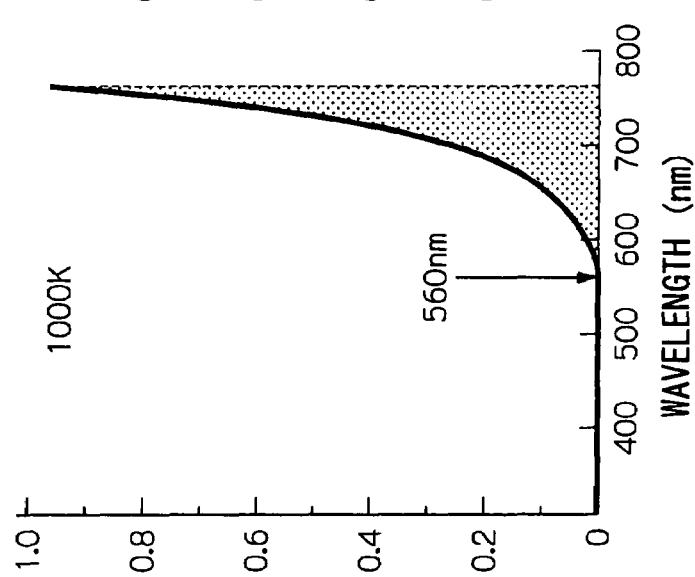
Figure 8C:
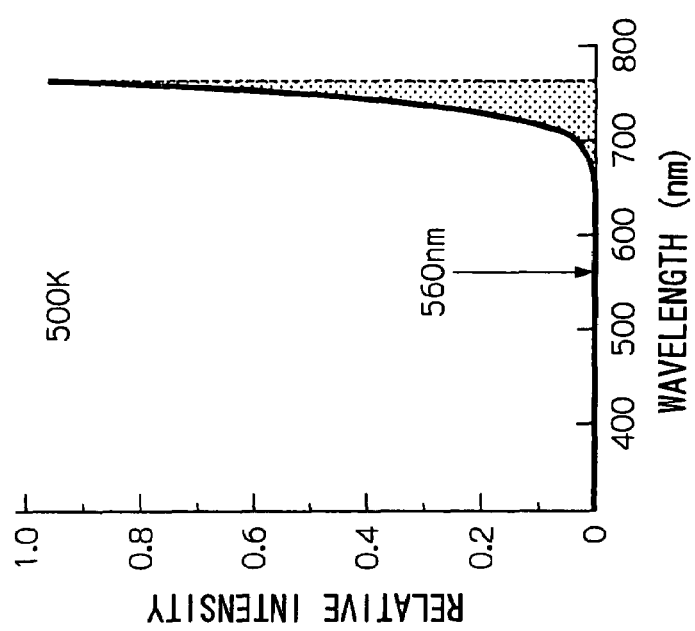

The wavelength of the light, which is irradiated in cases in which the temperature of the high-temperature portion of the flash lamp 38 is from 500 K to 1000 K, exceeds 560 nm as shown in FIG. 8A and FIG. 8B respectively corresponding to in a case of 500 K and in a case of 1000 K. The wavelength of the light, which is irradiated in cases in which the temperature of the high-temperature portion of the flash lamp 38 is 1500 K, exceeds 450 nm as shown in FIG. 8C.

Because there are few cases in which the temperature of the high-temperature portion of the flash lamp 38 exceeds 1000 K, the wavelength of the light emitted from the light-emitting portion 52 is made to be less than or equal to 560 nm, and the light-receiving portion 54 which is sensitive to light of this wavelength is used. More desirably, the wavelength of the light emitted from the light-emitting portion 52 is made to be less than or equal to 450 nm, and the light-receiving portion 54 which is sensitive to light of this wavelength is used.

Note that the wavelengths of the spectral characteristics of the light-emitting portion 52 and the light-receiving portion 54 may be made to be less than or equal to 560 nm, and preferably, less than or equal to 450 nm.

In this way, the light-receiving portion 54 does not sense the irradiated light from the flash lamps 38, and efficiently receives the scattered light which is emitted from the light-emitting portion 52 and scatters due to smoke.

Further, the region of the spectral characteristic of the light-emitting portion 52 is included in the region of the spectral characteristic of the light-receiving portion 54, and the peaks of the spectral characteristics of the light-emitting portion 52 and the light-receiving portion 54 are made to correspond and made to approximately same. In this way, the light-receiving portion 54 does not sense light which acts as noise from the exterior, and efficiently receives the scattered light which is emitted from the light-emitting portion 52 and scatters due to smoke.

The light-emitting portion 52, whose light-emitting frequency band is narrow to a certain extent, and the light-receiving portion 54, which is sensitive to a band which is narrow to a certain extent, are used. The half-value widths of the spectral characteristics of the light-emitting portion 52 and the light-receiving portion 54 are made to be less than or equal to 30 nm for example.

In this way, the light-receiving portion 54 does not sense light which acts as a noise from the exterior, and efficiently receives the scattered light which is emitted from the light-emitting portion 52 and scatters due to smoke.

Specifically, it is preferable to use a light-emitting diode (LED) or a laser diode (LD), whose light-emitting frequency band is narrow as compared with other light-emitting elements, as the light-emitting portion 52. In particular, a laser diode is suited to making the illumination angle of the light beam small and making the amount of illuminated light large, as compared with other light-emitting elements.

Figure 9:
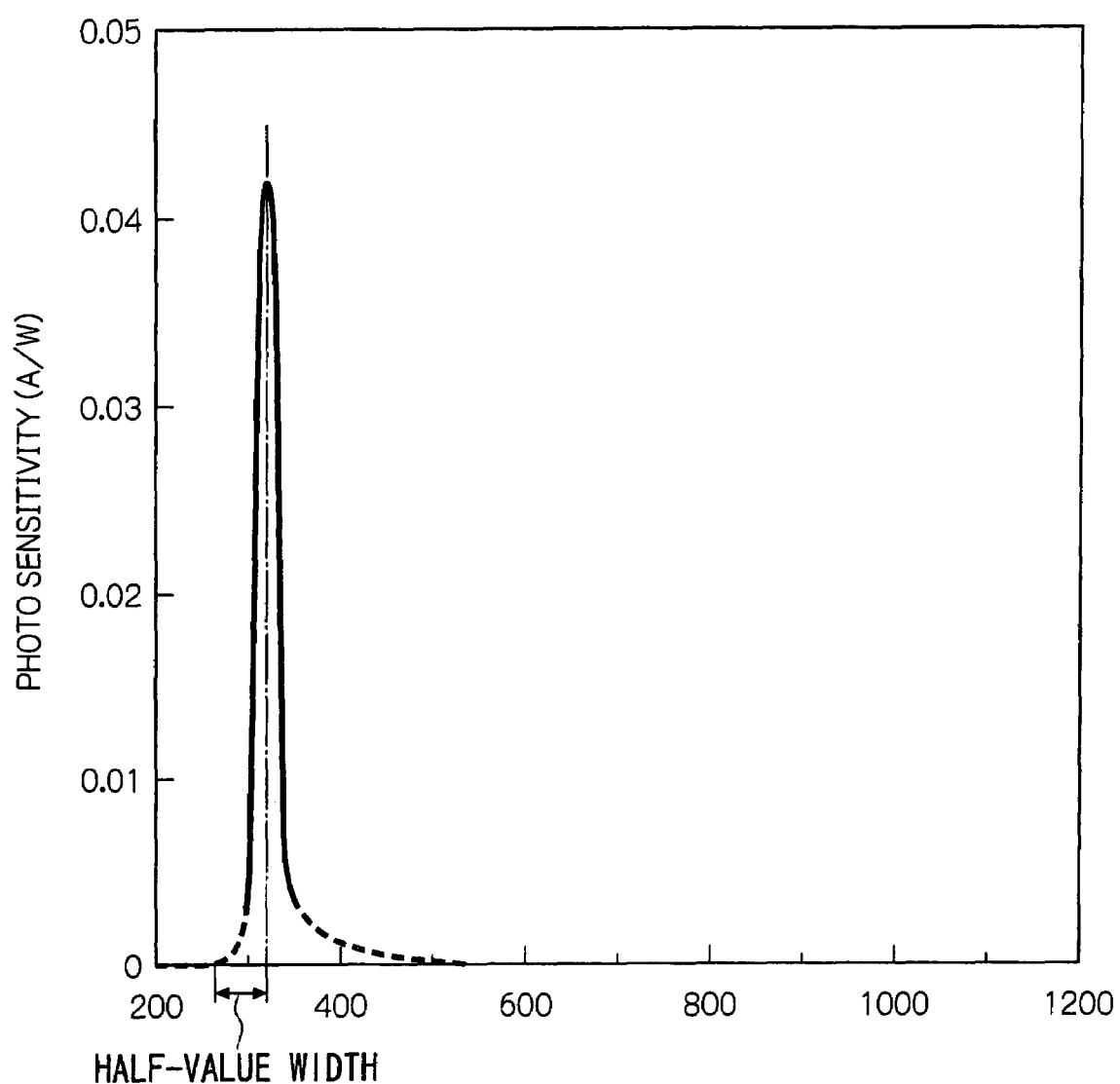
FIG. 9 is a drawing showing a spectral characteristic of a photodiode serving as a light-receiving portion relating to the present exemplary embodiment.

Further, as the light-receiving element 54 which is sensitive to a narrow band as compared with other light-receiving elements, it is preferable to use a photodiode or a PIN photodiode, which is sensitive to a narrow band as compared with other light-emitting elements. The spectral characteristic of a photodiode which is sensitive to a narrow band of near ultraviolet radiation is shown in FIG. 9. By using this photodiode and a light-emitting diode whose peak wavelength corresponds to that of the photodiode, only light of a single wavelength region is used.

Next, the processing device 58, which serves as the judging section which judges whether or not smoke is generated, will be described.

The processing device 58 acquires a light amount signal from the light-receiving portion 54, and, on the basis of this light amount signal, judges whether or not smoke is generated from the recording medium P. Specifically, for example, in a case in which the value of the light amount signal acquired from the light-receiving portion 54 reaches or exceeds a predetermined reference value, the processing device 58 judges that smoke is generated from the recording medium P.

When the flash lamps 38 emit light, there is the possibility that the light-receiving portion 54 will receive the flash-light from the flash lamps 38. Therefore, the processing device 58 judges whether or not smoke is generated, on the basis of the light amount signal of the light which the light-receiving portion 54 receives during a time period other than the time period when the flash-light is illuminated from the flash fusing device 30. Specifically, for example, the light-emitting portion 52 and the light-receiving portion 54 can be structured so as to not be operated during illumination time period of the flash fusing device 30. Further, a structure may be used in which the processing device 58 does not acquire the light amount signal of the light which the light-receiving portion 54 receives during illumination time period of the flash fusing device 30. Moreover, a structure may be used in which the processing device 58 acquires the light amount signal of the light which the light-receiving portion 54 receives during illumination time period of the flash fusing device 30, but does not carry out judgment on the basis of this light amount signal.

In a method of fixing by flash-light of the flash lamps 38, immediately after the flash lamps 38 emit light, smoke is generated due to decomposition of the toner on the recording medium P. The smoke due to this decomposition of the toner is normal smoke of a type which is allowable, and there is the need to differentiate it from smoke generated from the recording medium P.

Figure 10A:
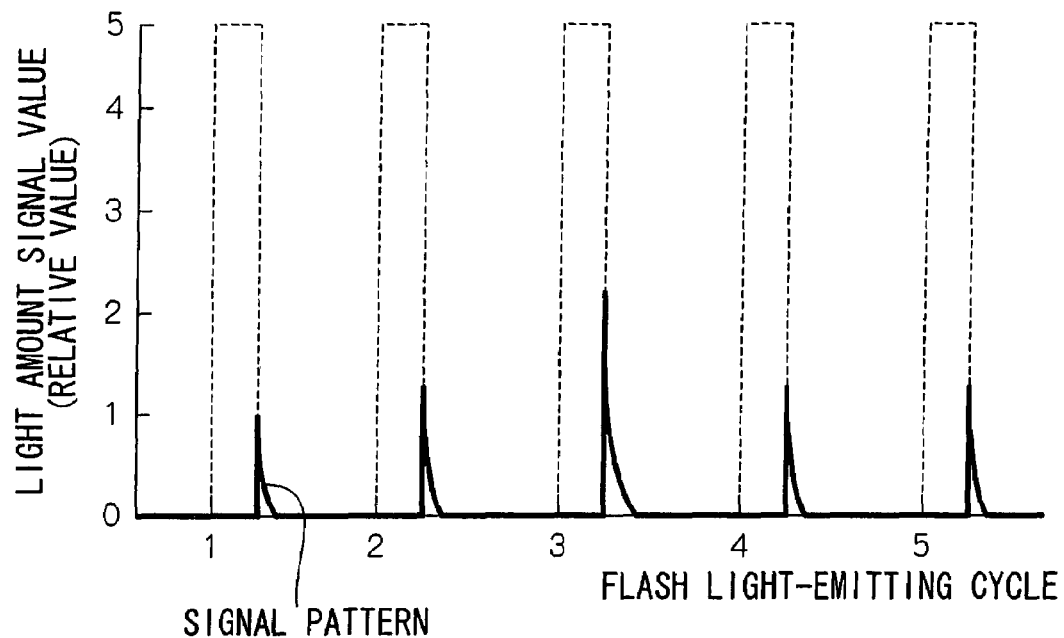
FIGS. 10A and 10B are drawings showing signal patterns formed by light amount signals acquired by a processing device relating to the present exemplary embodiment, where
Figure 10B:
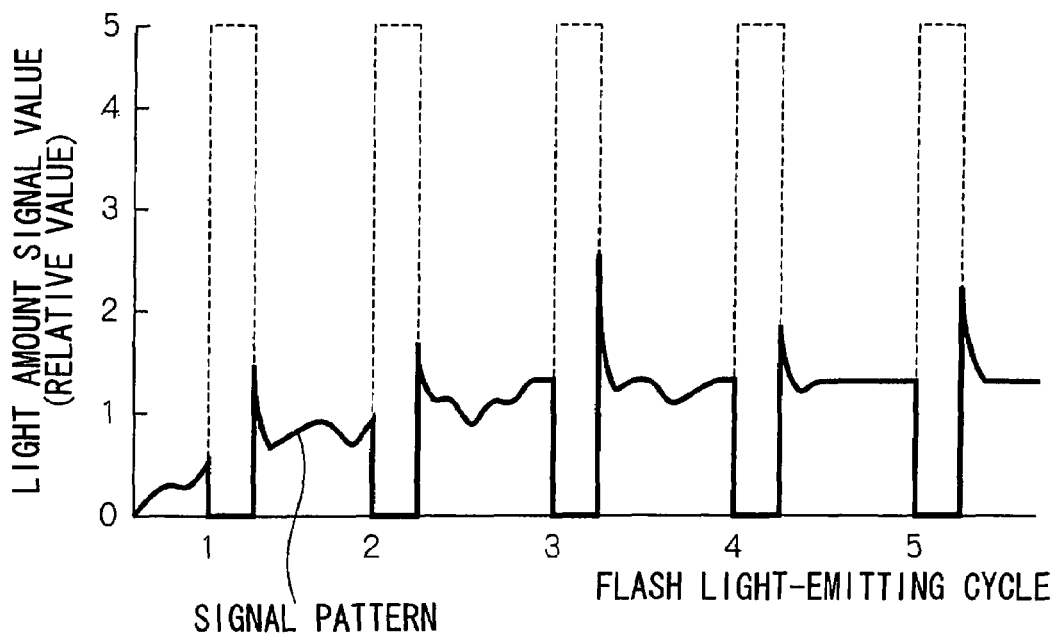

Immediately after the flash lamps 38 emit light, smoke caused by the decomposition of the toner is generated, and therefore, both at normal time when smoke is not generated from the recording medium P and at abnormal time when smoke is generated from the recording medium P, there are cases in which no large difference in the light amount of the scattered light received by the light-receiving portion 54 can be seen (refer to FIG. 10A and FIG. 10B).

Thus, in the present exemplary embodiment, whether or not smoke is generated is judged on the basis of the light amount signal of the light which the light-receiving portion 54 receives after a predetermined time period (e.g., 10 to 50 msec) has elapsed after the flash lamps 38 emit light.

Further, a structure may be used in which the processing device 58 forms a time-series signal pattern from the light amount signal of the light which the light-receiving portion 54 receives each time a predetermined time period elapses, and it is judged that smoke is generated in cases in which there is a predetermined difference in shape between this signal pattern and a reference pattern which is acquired in advance.

For example, as shown in FIG. 10A, a time-series signal pattern formed from light amount signals at a time when smoke is not generated, is used as the reference pattern. The processing device 58 stores this reference pattern in advance.

As shown in FIG. 10A, a time-series signal pattern, in which the height (light amount signal value) is high immediately after the flash fusing device 30 illuminates flash-light and the height gradually becomes lower, is formed at a time when smoke is not generated. As shown in FIG. 10B, a time-series signal pattern, in which the height is high immediately after the flash fusing device 30 illuminates flash-light and the height remains high even after time passes, is formed at a time when smoke is generated.

The processing device 58 compares the signal pattern, which is formed from the light amount signals acquired from the light-receiving portion 54, and the reference pattern, and judges that smoke is generated, for example, in a case in which the difference in heights of the shapes of the signal patterns is greater than or equal to a predetermined value.

Figure 11:
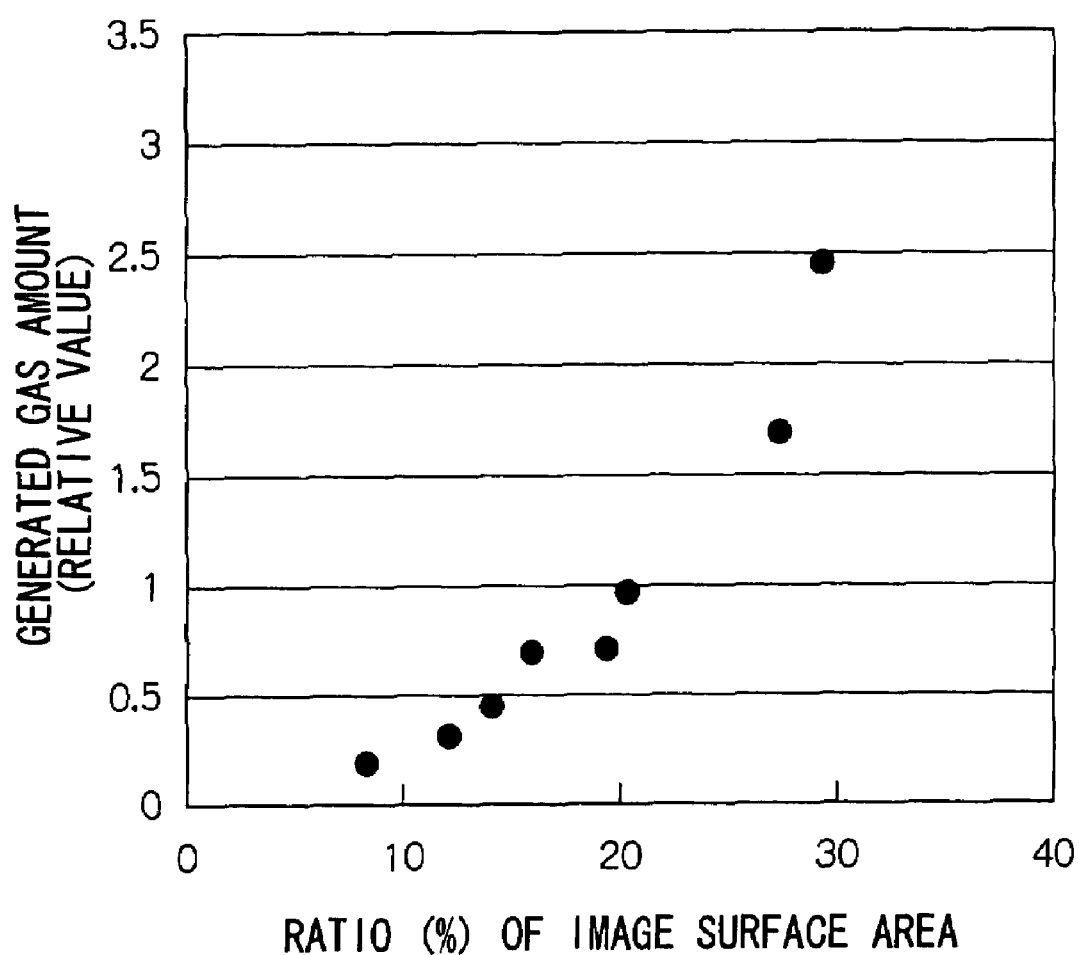
FIG. 11 is a drawing showing the relationship between a surface area ratio of a toner image relating to the present exemplary embodiment, and smoke (gas) which is generated.

Further, as shown in FIG. 11, the amount of smoke (gas) which is generated due to the toner decomposition varies in accordance with the surface area ratio of the formed toner image with respect to a predetermined unit surface area of the recording medium P. If the surface area of the toner image formed on the recording medium P is large, the amount of smoke which is generated also becomes large. Accordingly, in accordance with variations in the toner image, the amount of scattered light which scatters also varies, and the amount of light which the light-receiving portion 54 receives also varies.

Thus, in the present exemplary embodiment, the predetermined reference value is changed on the basis of the ratio of the surface area of the formed toner image with respect to a predetermined unit surface area of the recording medium P. If the value of the light amount signal reaches or exceeds the predetermined reference value, it is judged that smoke is generated in the illumination region S.

Figure 12:
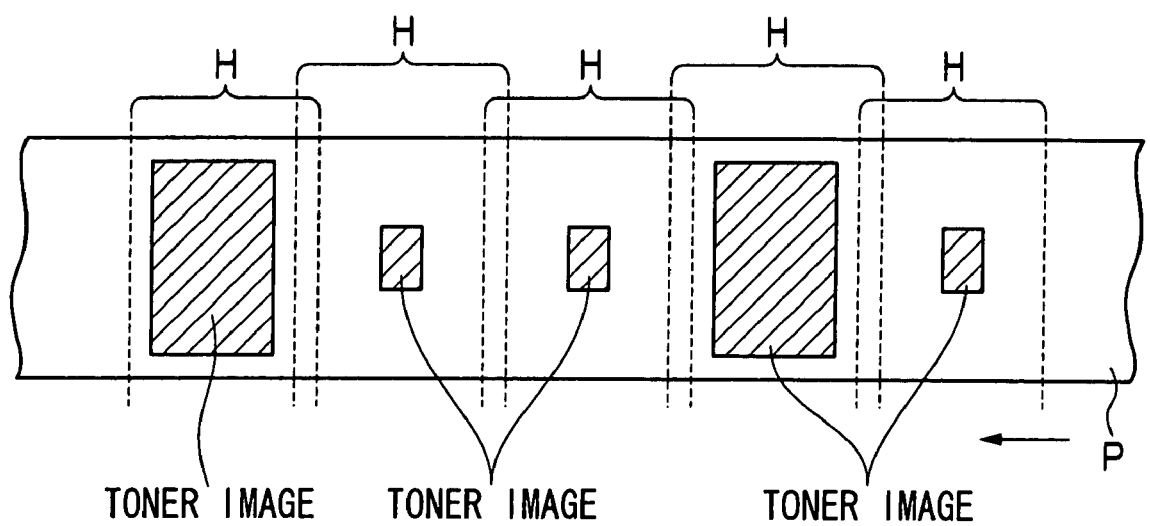
FIG. 12 is a drawing showing examples of surface areas of toner images formed on the recording medium relating to the present exemplary embodiment.

As shown in FIG. 12, the flash fusing device 30 illuminates the flash-light each predetermined range H of the recording medium P which is conveyed in the illumination region S, and the toner images are fixed on the recording medium P. In a case in which, as shown in FIG. 12, the toner images are different within the predetermined ranges H of the recording medium P at which the flash-light is illuminated, if the flash fusing device 30 illuminates the flash-light onto a portion where the aforementioned surface area ratio of the toner image is large, the predetermined reference value is set large such that even though the amount of generated smoke at this portion is greater than the amount of smoke generated at a portion where the aforementioned surface area ratio of the toner image is small, generation of smoke can be allowed.

Also in a case in which a signal pattern is formed and judgment is carried out, the reference pattern is revised on the basis of the surface area ratio of the toner image formed on the recording medium P, and the signal pattern and the revised reference pattern are compared.

The light amount detected due to abnormal smoke generation is a sudden burst, and is extremely unstable in the initial stage. Therefore, in order to prevent erroneous detection, the processing device 58 is structured so as to judge that smoke is generated in a case in which a value, which averages light amount signals acquired plural times from the light-receiving portion 54, reaches or exceeds a predetermined reference value. Even in cases in which a signal pattern is formed and judgment is carried out, it is desirable to form a signal pattern plural times and carry out judgment in accordance with a signal pattern in which these signal patterns are averaged.

Figure 13:
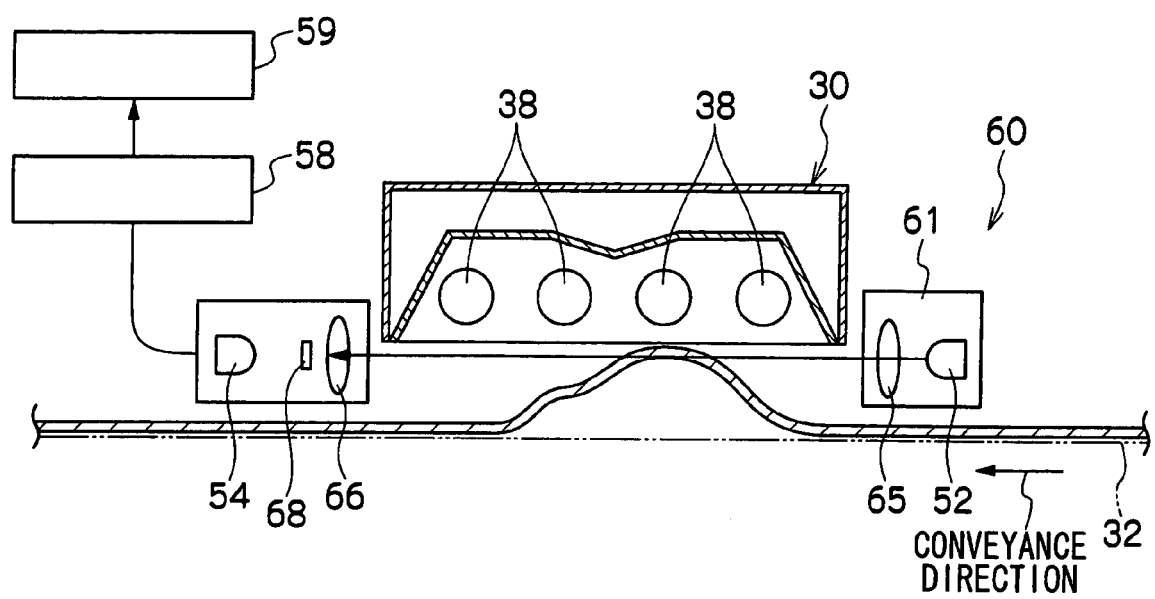
FIG. 13 is a drawing showing a case in which the recording medium has come off of a conveying path in the smoke detecting device relating to the present exemplary embodiment.

Further, as shown in FIG. 13, when the recording medium P comes off of the conveying path 32 due to the recording medium P rising-up or the like, the light L from the light-emitting portion 52 diffuses and is transmitted through the recording medium P, and this transmitted light is incident on the light-receiving portion 54. The light amount of this transmitted light is greater than the light amount of the scattered light which is scattered by smoke and incident on the light-receiving portion 54.

In a case in which the value of the light amount signal acquired from the light-receiving portion 54 reaches or exceeds a predetermined reference value which is higher than the aforementioned predetermined reference value, the processing device 58 judges that the recording medium P has come off of the conveying path 32.

A structure may be used in which a limiter for the received light amount is provided at the light-receiving portion 54, and when a light amount which exceeds the value of the limiter is received, a signal is transmitted to the processing device 58, and when the processing device 58 acquires this signal, the processing device 58 judges that the recording medium P has come off of the conveying path 32.

Note that, in the structure of the smoke detecting device 50, if the recording medium P comes off of the conveying path 32, the reflected light, which is the light L from the light-emitting portion 52 being diffused and reflected by the recording medium P, is incident on the light-receiving portion 54. The light amount of this reflected light as well is greater than the light amount of the scattered light which is scattered by smoke and incident on the light-receiving portion 54. In a case in which the value of the light amount signal acquired from the light-receiving portion 54 reaches or exceeds a predetermined reference value which is higher than the aforementioned predetermined reference value, the processing device 58 judges that the recording medium P has come off of the conveying path 32.

The processing device 58 is connected to the driving control section 36 of the flash fusing device 30. When the processing device 58 judges that smoke is generated, the processing device 58 sends smoke generation information to the driving control section 36, and stops the supply of electricity to the flash fusing device 30. Further, also in cases in which it is judged that the recording medium P has come off of the conveying path 32, similarly, the processing device 58 stops the supply of electricity to the flash fusing device 30.

A warning device 59 which warns is connected to the processing device 58. When the processing devices 58 judges that smoke is generated, the processing device 58 sends smoke generation information to the warning device 59, and the warning device 59 warns the exterior that smoke is generated. Further, also in cases in which it is judged that the recording medium P has come off of the conveying path 32, similarly, the warning device 59 warns the exterior that the recording medium P has come off of the conveying path 32.

The warning device 59 may be, for example, a display device which notifies the operator by displaying a warning on a display screen, or may be a notification device which notifies the operator by a warning sound or by a voice.

A modified example, in which plural sets of the light-emitting portion 52 and the light-receiving portion 54 are provided at predetermined intervals along the conveying path 32, will be described next.

Figure 14:
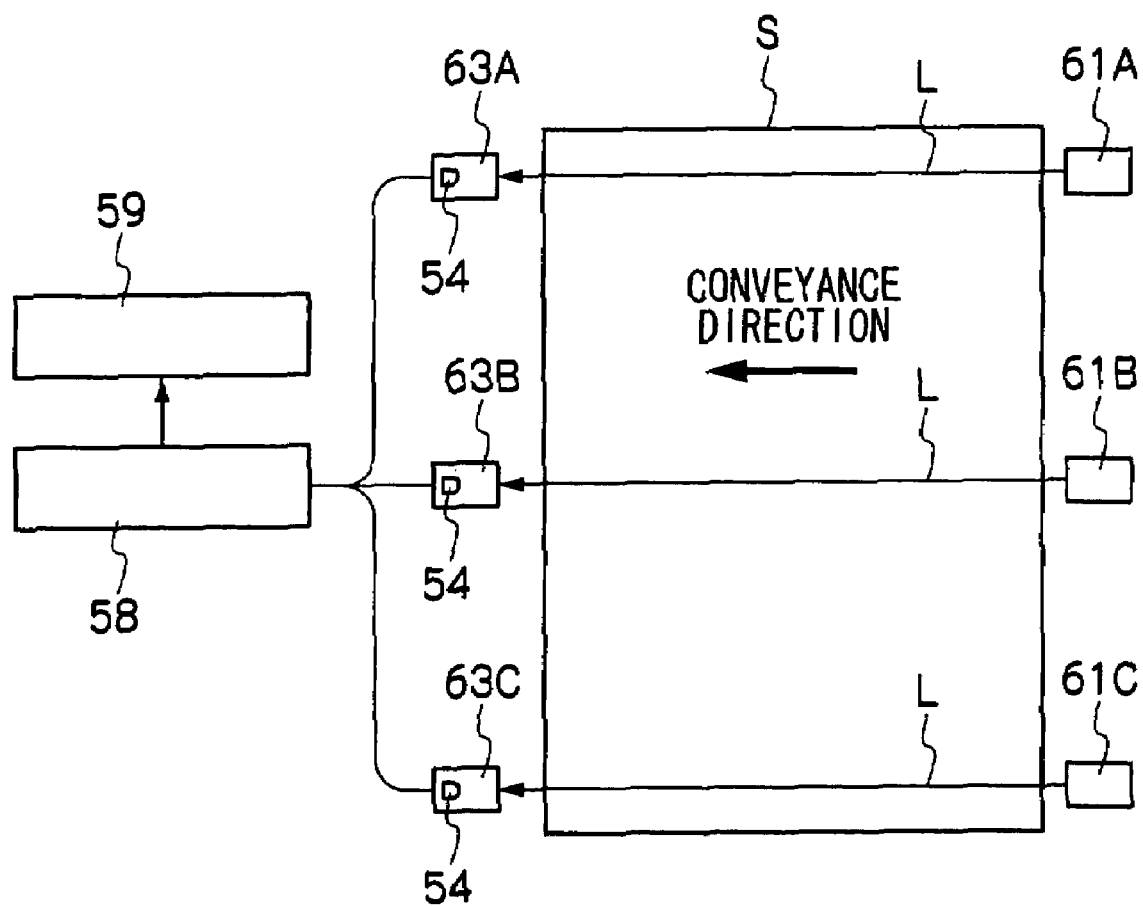
FIG. 14 is a drawing showing a structure in which plural sets of the light-emitting portion and the light-receiving portion relating to the present exemplary embodiment are provided.

As shown in FIG. 14, plural sets of light-emitting devices 61A, 61B, 61C and light-receiving devices 63A, 63B, 63C are provided at predetermined intervals. The respective sets of the light-emitting devices 61A, 61B, 61C and the light-receiving devices 63A, 63B, 63C are disposed such that emission directions of lights L in the respective sets are along the conveying direction of the recording medium P.

In this structure, the processing device 58 is connected to the respective light-receiving devices 63A, 63B, 63C, and acquires light amount signals from the light-receiving portions 54 of the light-receiving devices 63A, 63B, 63C. The processing device 58 acquires the light amount signals from the light-receiving portions 54, and on the basis of the light amount signals, judges whether or not smoke is generated from the recording medium P. Specifically, for example, if the value of the light amount signal acquired from the light-receiving portion 54 reaches or exceeds a predetermined reference value, the processing device 58 judges that smoke is generated at the recording medium P.

In this way, even in a case in which smoke is generated locally, such as, for example, a case in which smoke is generated from a residual piece of the recording medium P or the like, the value of the light amount signal of the light incident on any of the light-receiving portions 54 of the light-receiving devices 63A, 63B, 63C reaches or exceeds a predetermined reference value, and the processing device 58 judges that smoke is generated. Further, the processing device 58 specifies the position where the smoke is generated, by specifying at least one light-receiving device (among the light-receiving device 63A, 63B and 63C) at which the value of the light amount signal of the light-receiving portion 54 thereof reaching or exceeding the predetermined reference value.

Figure 15A:
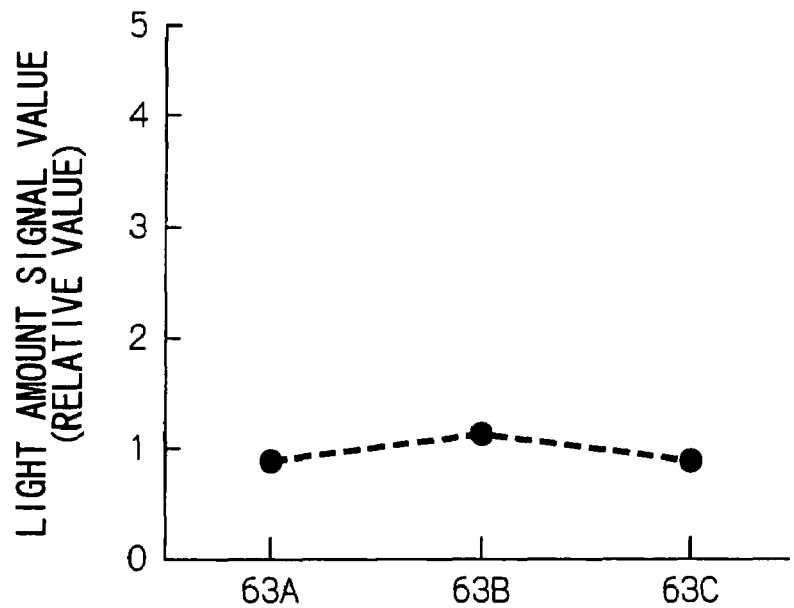
FIGS. 15A and 15B are drawings showing signal patterns formed by light amount signals which the processing device acquires in a structure in which plural sets of the light-emitting portion and the light-receiving portion relating to the present exemplary embodiment are provided, where
Figure 15B:
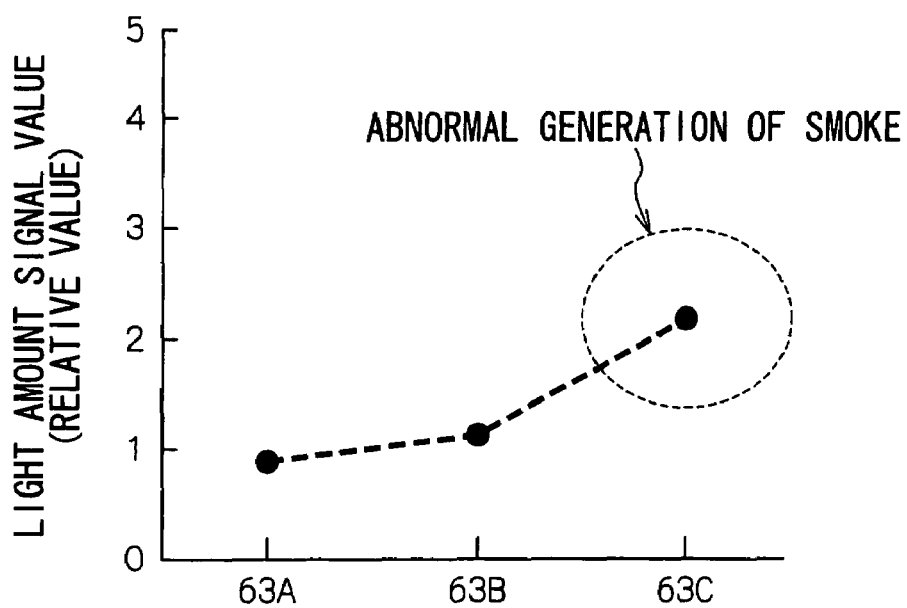

For example, as shown in FIG. 15B, if the light amount incident on the light-receiving portion 54 of the light-receiving device 63C is great, it can be understood that smoke is generated at the end portion of the recording medium P which is at the side where the light-emitting device 61C and the light-receiving device 63C are located.

When the processing device 58 specifies the position where smoke is generated, the processing device 58 sends position information to the warning device 59, and the warning device 59 notifies the operator.

Further, the processing device 58 may be structured so as to form a signal pattern from the light amount signals of the lights received by the light-receiving portions 54 of the respective light-receiving devices 63A, 63B, 63C, and to judge that smoke is generated in a case in which the signal pattern has a predetermined difference in shape with respect to a reference pattern which is acquired in advance.

A signal pattern, which is formed from the light amount signals at the time when smoke is not generated, such as shown in FIG. 15A for example, is used as the reference pattern. The processing device 58 stores this reference pattern in advance.

At the time when smoke is not generated, as shown in FIG. 15A, all of the light amounts incident on the light-receiving portions 54 of the respective light-receiving devices 63A, 63B, 63C do not have a great difference, and a flat signal pattern is formed.

At the time when smoke is generated, as shown in FIG. 15B, the light amount incident on the light-receiving portion 54 of any one of the light-receiving device 63A, 63B, 63C which is near to the position where smoke is generated, increases, and a signal pattern in which the height is high at a specific place is formed.

The processing device 58 compares the signal pattern which is formed from the light amount signals acquired from the light-receiving portions 54, and the reference pattern, and judges that smoke is generated in a case in which, for example, the difference in the heights of the signal pattern shapes is greater than or equal to a predetermined value.

Further, on the basis of the light amount signals acquired from the light-receiving portions 54 of the respective light-receiving devices 63A, 63B, 63C, the processing device 58 may form the above-described time-series signal pattern, and judge whether or not smoke is generated. Moreover, the processing device 58 may be structured so as to judge whether or not smoke is generated by combining this time-series signal pattern and the signal pattern formed by the light amount signals acquired from the light-receiving portions 54 of the respective light-receiving devices 63A, 63B, 63C.

Figure 16A:
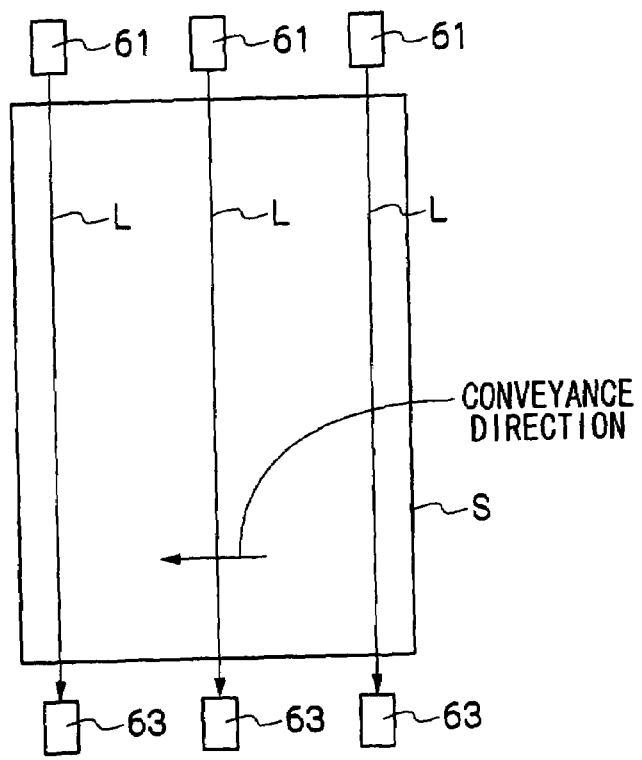
FIGS. 16A and 16B are drawings showing modified examples of structures in which plural sets of the light-emitting portion and the light-receiving portion relating to the present exemplary embodiment are provided, where
Figure 16B:
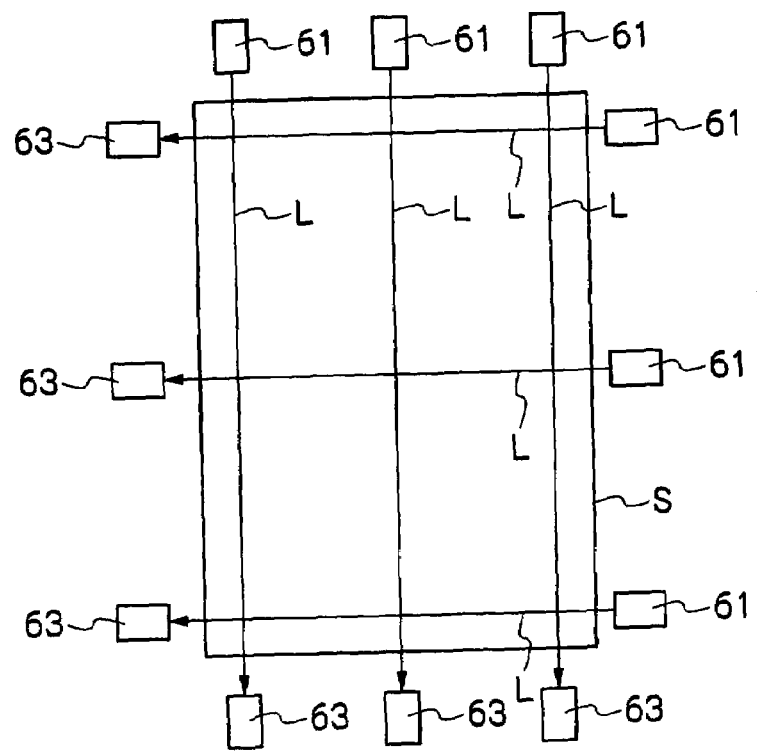

Note that, as shown in FIG. 16A, plural sets of light-emitting devices 61 and light-receiving devices 63 are provided at predetermined intervals. The respective sets of the light-emitting devices 61 and the light-receiving devices 63 are disposed such that emission directions of lights L in the respective sets are along a direction perpendicular to the conveying direction of the recording medium P. Further, as shown in FIG. 16B, a structure may be used in which the plural sets of the light-emitting devices 61 and the light-receiving devices 63 are disposed in the form of a grid, i.e., plural sets are disposed at predetermined intervals along the direction orthogonal to the conveying direction of the recording medium P, and plural sets are disposed at predetermined intervals along the conveying direction of the recording medium P.

The structure of the light-emitting devices 61 and the light-receiving devices 63 being disposed in plural rows may similarly be applied to a structure in which the light-emitting device 61 and the light-receiving device 63 are provided so as to be lined-up next to each other, i.e., in the smoke detecting device 50 shown in FIGS. 7A and 7B as well.

Operation of the above-described exemplary embodiment will be described next.

In accordance with the smoke detecting device 60 relating to the present exemplary embodiment, the light-emitting portion 52 emits light along the conveying path 32 which conveys the recording medium P. The light emitted by the light-emitting portion 52 hits smoke generated from the recording medium P and scatters. This scattered light is incident on the light-receiving portion 54, and the light-receiving portion 54 receives the scattered light.

At this time, among the light L which the light-emitting portion 52 emits, the direct light which passes-through without scattering is collected by the condenser lens 66, is shielded by the light-shielding plate 68, and is not incident on the light-receiving portion 54.

Note that, in the case of the smoke detecting device 50, among the light which the light-emitting portion 52 emits, the light which passes-through without scattering is absorbed at the light absorbing device 56, and is not incident on the light-receiving portion 54.

The spectral characteristics of the light which the light-emitting portion 52 emits and the light which the light-receiving portion 54 receives are set such that the light-receiving portion 54 is sensitive to the light which is emitted from the light-emitting portion 52. Therefore, the light-receiving portion 54 does not sense light from the exterior such as the irradiated light from the flash lamps 38 or the like, and efficiently receives the scattered light.

The processing device 58 acquires, from the light-receiving portion 54, the light amount signal of the light which the light-receiving portion 54 receives. If the value of this light amount signal reaches or exceeds a predetermined reference value, the processing device 58 judges that smoke is generated from the recording medium P.

At this time, the processing device 58 judges whether or not smoke is generated on the basis of the light amount signal of the light that the light-receiving portion 54 receives at a time period other than the time period when the flash-light is illuminated from the flash fusing device 30.

When the processing device 58 judges that smoke is generated, the processing device 58 sends smoke generation information to the driving control section 36 and stops the supply of electricity to the flash fusing device 30. Further, the processing device 58 sends smoke generation information to the warning device 59, and the warning device 59 warns the exterior that smoke is generated.

The present invention is not limited to the present exemplary embodiment, and various modifications, changes and improvements are possible without deviating from the gist of the present invention.

What is claimed is:

1. A smoke detecting device comprising:
   a light-emitting portion that emits light;
   a light-receiving portion that receives scattered light resulting from the light which the light-emitting portion emits being scattered by smoke generated from a recording medium on which flash-light is irradiated from a flash fusing device; and
   a judging section that acquires a light amount signal of the received light, from the light-receiving portion, and that judges, on the basis of the light amount signal, whether or not smoke has been generated from the recording medium on which flash-light is irradiated from the flash fusing device, and the judging section judges that smoke has been generated from the recording medium in a case in which a value of the light amount signal reaches a predetermined reference value, the judging section changing the predetermined reference value in accordance with a ratio of an area of a formed toner image on the recording medium with respect to a predetermined unit area of the recording medium; and
   the light that the light-emitting portion emits passing through a space between the flash fusing device and the recording medium.

2. A smoke detecting device comprising:
   a light-emitting portion that emits light;
   a light-receiving portion that receives scattered light resulting from the light which the light-emitting portion emits being scattered by smoke generated from a recording medium on which flash-light is irradiated from a flash fusing device; and
   a judging section that acquires a light amount signal of the received light, from the light-receiving portion, and that judges, on the basis of the light amount signal, whether or not smoke has been generated from the recording medium on whose bottom surface the flash-light is irradiated from the flash fusing device, and the judging section judges that smoke has been generated from the recording medium in a case in which a value of the light amount signal reaches a predetermined reference value, the judging section changing the predetermined reference value in accordance with a ratio of an area of a formed toner image on the recording medium with respect to a predetermined unit area of the recording medium; and the light that the light-emitting portion emits passing at a side of the recording medium opposite a side at which the flash fusing device is located.

3. The smoke detecting device of claim 1, wherein the judging section judges whether or not smoke has been generated on the basis of the light amount signal of light which the light-receiving portion receives at a time period other than a time period when the flash-light is irradiated from the flash fusing device.

4. The smoke detecting device of claim 1, wherein the judging section judges that smoke has been generated in a case in which a value, which is obtained by averaging light amount signals acquired a plurality of times from the light-receiving portion, reaches a predetermined reference value.

5. The smoke detecting device of claim 1, wherein the judging section judges whether or not smoke has been generated on the basis of the light amount signal of light which the light-receiving portion receives after the flash fusing device irradiates the flash-light and a predetermined time period elapses.

6. The smoke detecting device of claim 1, wherein the judging section forms a time-series signal pattern from the light amount signals of light which the light-receiving portion receives each time a predetermined time period elapses, and, if the time-series signal pattern has a predetermined difference in shape with respect to a reference pattern which is acquired in advance, the judging section judges that smoke has been generated.

7. The smoke detecting device of claim 1, wherein:
a plurality of sets of the light-emitting portion and the light-receiving portion are provided; and
the judging section acquires light amount signals from the light-receiving portions, and, on the basis of values of the light amount signals, specifies a position where smoke has been generated.

8. The smoke detecting device of claim 7, wherein the judging section forms a signal pattern from the light amount signals acquired from the plurality of light-receiving portions, and, if the signal pattern has a predetermined difference in shape with respect to a reference pattern which is acquired in advance, the judging section judges that smoke has been generated.

9. The smoke detecting device of claim 1, wherein a wavelength of the light that the light-emitting portion emits is less than or equal to 560 nm.

10. The smoke detecting device of claim 1, wherein a wavelength of the light that the light-emitting portion emits is less than or equal to 450 nm.

11. The smoke detecting device of claim 1, wherein a region of a spectral characteristic of the light-emitting portion is included in a region of a spectral characteristic of the light-receiving portion.

12. The smoke detecting device of claim 1, wherein:
the light-receiving portion receives transmitted light transmitted through or reflected light reflected by the recording medium which has come off of a conveying path; and
the judging section acquires the light amount signal of the received light, from the light-receiving portion, and judges, on the basis of the light amount signal, whether or not the recording medium has come off of the conveying path.

13. The smoke detecting device of claim 12, wherein the judging section judges whether or not smoke has been generated from the recording medium and whether or not the recording medium has come off of the conveying path by comparing the received light amount with a first reference value and a second reference value that is larger than the first reference value.

14. The smoke detecting device of claim 7, wherein, in each set, the light-emitting portion and the light-receiving portion are disposed such that an emission direction of the light that the light-emitting portion emits is along a conveying direction of the recording medium.

15. The smoke detecting device of claim 1, further comprising:
a light collecting portion that is disposed between the light-emitting portion and the light-receiving portion and near the light-receiving portion, and that collects light incident thereto; and
a light shielding portion that shields light,
wherein the light collecting portion collects the scattered light, at the light-receiving portion, and collects the light which the light-emitting portion emits and is not scattered, at the light shielding portion.

16. A flash fusing device comprising:
a smoke detecting device including:
a light-emitting portion that emits light,
a light-receiving portion that receives scattered light resulting from the light which the light-emitting portion emits being scattered by smoke generated from a recording medium on which flash-light is irradiated from the flash fusing device, and
a judging section that acquires a light amount signal of the received light, from the light-receiving portion, and that judges, on the basis of the light amount signal, whether or not smoke has been generated from the recording medium on which flash-light is irradiated from the flash fusing device, the light that the light-emitting portion emits passing through a space between the flash fusing device and the recording medium, and the judging section judges that smoke has been generated from the recording medium in a case in which a value of the light amount signal reaches a predetermined reference value, the judging section changing the predetermined reference value in accordance with a ratio of an area of a formed toner image on the recording medium with respect to a predetermined unit area of the recording medium; and
a blower device that sends air to an irradiation region at which the flash fusing device irradiates the flash-light, the light-emitting portion emitting light along a blowing direction in which the blower device sends air.

17. An image forming device comprising:
a flash fusing device that fixes an image on a recording medium by irradiating flash-light; and
a smoke detecting device including:
a light-emitting portion that emits light,
a light-receiving portion that receives scattered light resulting from the light which the light-emitting portion emits being scattered by smoke generated from the recording medium on which the flash-light is irradiated from the flash fusing device, and
a judging section that acquires a light amount signal of the received light, from the light-receiving portion, and that judges, on the basis of the light amount signal, whether or not smoke has been generated from the recording medium on which the flash-light is irradiated from the flash fusing device, and the judging section judges that smoke has been generated from the recording medium in a case in which a value of the light amount signal reaches a predetermined reference value, the judging section changing the predetermined reference value in accordance with a ratio of an area of a formed toner image on the recording medium with respect to a predetermined unit area of the recording medium;

the light that the light-emitting portion emits passing through a space between the flash fusing device and the recording medium.

18. A smoke detecting method comprising:

receiving scattered light resulting from emitted light being scattered by smoke generated from a recording medium on which flash-light is irradiated from a flash fusing device, the emitted light passing through a space between the flash fusing device and the recording medium;

acquiring a light amount signal of the received light;

judging, on the basis of the light amount signal, whether or not smoke has been generated from the recording medium on which flash-light is irradiated from the flash fusing device; and in a case in which a value of the light amount signal reaches a predetermined reference value, changing the predetermined reference value in accordance with a ratio of an area of a formed toner image on the recording medium with respect to a predetermined unit area of the recording medium.

* * * * *